(12) United States Patent
Rasenick et al.

(10) Patent No.: US 8,062,874 B2
(45) Date of Patent: Nov. 22, 2011

(54) GFP FUSION PROTEINS AND THEIR USE

(75) Inventors: Mark Rasenick, Glenview, IL (US); Jiang-zhou Yu, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 995 days.

(21) Appl. No.: 10/482,980

(22) PCT Filed: Jul. 3, 2002

(86) PCT No.: PCT/US02/21484
§ 371 (c)(1),
(2), (4) Date: Sep. 22, 2004

(87) PCT Pub. No.: WO03/008435
PCT Pub. Date: Jan. 30, 2003

(65) Prior Publication Data
US 2006/0247418 A1    Nov. 2, 2006

Related U.S. Application Data

(60) Provisional application No. 60/303,622, filed on Jul. 6, 2001.

(51) Int. Cl.
C12N 9/00 (2006.01)
C12N 9/12 (2006.01)
C07K 1/00 (2006.01)
C12P 21/08 (2006.01)
G01N 33/53 (2006.01)

(52) U.S. Cl. .......... 435/183; 435/194; 435/7.1; 435/7.6; 530/350; 530/387.3

(58) Field of Classification Search .................. None
See application file for complete search history.

(56) References Cited

U.S. PATENT DOCUMENTS

| 5,625,048 A | 4/1997 | Tsien et al. |
| 5,683,888 A | 11/1997 | Campbell et al. |
| 5,976,796 A | 11/1999 | Szalay et al. |

FOREIGN PATENT DOCUMENTS

| WO | 9814605 | 4/1998 |
| WO | 9821355 | 5/1998 |
| WO | 9836081 | 8/1998 |

OTHER PUBLICATIONS

Ngo et al., In the Protein Folding Problem and Tertiary Structure Prediction, 1994, Merz et al. (ed.), Birkhauser, Boston; MA, pp. 433 and 492-495.*
Hughes et al., Journal of Biological Chemistry, 2001, vol. 276(6): 4227-4235.*
Yuan et al., Journal of Biological Chemistry, 2000, 275(3): 2157-2164.*
Milligan et al., Heterotrimeric G-proteins: a short history, British Journal of Pharmacology, 2006, 147: S46-S55.*
Meszaros et al., Identification of G protein-coupled signaling pathways in cardiac fibroblasts: cross talk between Gq and Gs, Am. J. Physiol. Cell Physiol., 2000, 278: C154-C162.*
Levis et al., Activation of the alpha subunit of Gs in intact cells alters its abundance, rate of degradation, and membrane avidity, Journal of Cell Biology, 1992, vol. 119, No. 5, pp. 1297-1307.*
Liu et al., The helical domain of a G protein subunit is a regulator of its effector, Proc. Natl. Acad. Sci., 1998, vol. 95, pp. 12878-12883.*
Blast 2 Sequences, sequence alignment results. Retrieved from the Internet <URL:http://www.ncbi.nlm.nih.gov/blast/bl2seq/wblast2.cgi>, last viewed on Mar. 24, 2008.*
Antonelli et al. (Human-Xenopus chimeras of Gs reveal a new region important for its activation of adenylyl cyclase, FEBS Letters, 340 (1994), pp. 249-254).*
Yu, Y.Z. (2002) "Real-timeVisualization of a Fluorescent Galphas: Dissociation of the Activated G Protein from plasma Membrane." *Molecular Pharmacology.* vol. 61. No. 2: 352-359.
Goto, Katsutoshi, et. al. (2000) "Subtype-Specific Trafficking of Endothelin Receptors." *Journal of Biological Chemistry.* vol. 275. No. 12: 8664-8671.
Kitamura, Toshio, et. al. (2000) "A Method to Identify cDNAs based on localization of Green Fluorescent Protein Fusion Products." *Proceedings of the National Academy of Sciences of the United States of America.* vol. 97. No. 7: 3062-3066.
Siegel, M.S., et. al. (1997) "A Genetically Encoded Optical Probe of Membrane Voltage." *Neuron.* vol. 19. No. 4: 735-741.
Liu, J., et. al. (1997) "The First 35 Amino Acids and Fatty Acylation Sites Determine the Molecular Targeting of Endothelial Nitric Oxide Synthase into the Golgi Region of Cells: A Green Fluorescent Protein Study." *Journal of Cell Biology.* vol. 137. No. 7: 1525-1535.
Biondi, R.M., et. al. (1998) "Random Insertion of GFP into the cAMP-Dependent Protein Kinase Regulatory Subunit from *Dictyostelium discoideum.*" *Nucleic Acids Research.* vol. 26. No. 21: 4946-4952.
Kudo, N., et. al. (1997) "Molecular Cloning and Cell Cycle-Dependent Expression of Mammalian CRM1, a Protein Involved in Nuclear Export of Proteins." *J. Biol. Chem.* vol. 272. No. 47: 29742-29751.
Romoser, V.A., et. al. (1997) "Detection in Living Cells of Ca Super (2+)-Dependent Changes in the Fluorescence Emission of an Indicator Composed of Two Green Fluorescent Protein Variants Linked by a Calmodulin-Binding Sequence. A New Class of Fluorescent Indicators." *J. Biol. Chem.* vol. 272. No. 20: 13270-13274.

* cited by examiner

*Primary Examiner* — David J Steadman
*Assistant Examiner* — Jae W Lee
(74) *Attorney, Agent, or Firm* — Barnes & Thornburg LLP; Alice O. Martin

(57) ABSTRACT

The present invention provides fusion proteins including a green fluorescent protein inserted into the internal amino acid sequence of a Gαs protein and further provides method of using the fusion protein construct to follow activation of a G-protein receptor by a candidate drug.

8 Claims, 11 Drawing Sheets

COS-1

PC12

HEK 293

FIG.9A

AAGCTTGC<u>CATG</u>GGCTGCCTCGGCAACAGTAAGACCGAGGACCAGCGCAACGAGGAGAAGGCGCAGCGCGAGGCCAACAAAAAGATCGAG
TTCGAACGGTACCCGACGGAGCCGTTGTCATTCTGCTGGGCTCTCGCGTTGCTCCTCTTCCGCGTCGCGCTCCGGTTGTTTTTCTAGCTC
      MetGlyCysLeuGlyAsnSerLysThrGluAspGlnArgAsnGluGluLysAlaGlnArgGluAlaAsnLysLysIleGlu

AAGCAGCTGCAGAAGGACAAGCAGGTCTACCGGGCCACGCACCGCCTGCTGCTGCTGGGTGCTGGAGAGTCTGGCAAAAGCACCATTGTG
TTCGTCGACGTCTTCCTGTTCGTCCAGATGGCCCGGTGCGTGGCGGACGACGACGACCCACGACCTCTCAGACCGTTTTCGTGGTAACAC
LysGlnLeuGlnLysAspLysGlnValTyrArgAlaThrHisArgLeuLeuLeuLeuGlyAlaGlyGluSerGlyLysSerThrIleVal

AAGCAGATGAGGATCCTACATGTTAATGGGTTTAACGGAGAGGGCGGCGAAGAGGACGAATTCGCCACCATGGTGAGCAAGGGCGAGGAG
TTCGTCTACTCCTAGGATGTACAATTACCCAAATTGCCTCTCCCGCCGCTTCTCCTGCTTAAGCGGTGGTACCACTCGTTCCCGCTCCTC
LysGlnMetArgIleLeuHisValAsnGlyPheAsnGlyGluGlyGlyGluGluAspGluPheAlaThrMetValSerLysGlyGluGlu

CTGTTCACCGGGGTGGTGCCCATCCTGGTCGAGCTGGACGGCGACGTAAACGGCCACAAGTTCAGCGTGTCCGGCGAGGGCGAGGGCGAT
GACAAGTGGCCCCACCACGGGTAGGACCAGCTCGACCTGCCGCTGCATTTGCCGGTGTTCAAGTCGCACAGGCCGCTCCCGCTCCCGCTA
LeuPheThrGlyValValProIleLeuValGluLeuAspGlyAspValAsnGlyHisLysPheSerValSerGlyGluGlyGluGlyAsp

GCCACCTACGGCAAGCTGACCCTGAAGTTCATCTGCACCACCGGCAAGCTGCCCGTGCCCTGGCCCACCCTCGTGACCACCCTGACCTAC
CGGTGGATGCCGTTCGACTGGGACTTCAAGTAGACGTGGTGGCCGTTCGACGGGCACGGGACCGGGTGGGAGCACTGGTGGGACTGGATG
AlaThrTyrGlyLysLeuThrLeuLysPheIleCysThrThrGlyLysLeuProValProTrpProThrLeuValThrThrLeuThrTyr

GGCGTGCAGTGCTTCAGCCGCTACCCCGACCACATGAAGCAGCACGACTTCTTCAAGTCCGCCATGCCCGAAGGCTACGTCCAGGAGCGC
CCGCACGTCACGAAGTCGGCGATGGGGCTGGTGTACTTCGTCGTGCTGAAGAAGTTCAGGCGGTACGGGCTTCCGATGCAGGTCCTCGCG
GlyValGlnCysPheSerArgTyrProAspHisMetLysGlnHisAspPhePheLysSerAlaMetProGluGlyTyrValGlnGluArg

ACCATCTTCTTCAAGGACGACGGCAACTACAAGACCCGCGCCGAGGTGAAGTTCGAGGGCGACACCCTGGTGAACCGCATCGAGCTGAAG
TGGTAGAAGAAGTTCCTGCTGCCGTTGATGTTCTGGGCGCGGCTCCACTTCAAGCTCCCGCTGTGGGACCACTTGGCGTAGCTCGACTTC
ThrIlePhePheLysAspAspGlyAsnTyrLysThrArgAlaGluValLysPheGluGlyAspThrLeuValAsnArgIleGluLeuLys

FIG. 9B

GGCATCGACTTCAAGGAGGACGGCAACATCCTGGGGCACAAGCTGGAGTACAACTACAACAGCCACAACGTCTATATCATGGCCGACAAG
CCGTAGCTGAAGTTCCTCCTGCCGTTGTAGGACCCCGTGTTCGACCTCATGTTGATGTTGTCGGTGTTGCAGATATAGTACCGGCTGTTC
GlyIleAspPheLysGluAspGlyAsnIleLeuGlyHisLysLeuGluTyrAsnTyrAsnSerHisAsnValTyrIleMetAlaAspLys

CAGAAGAACGGCATCAAGGTGAACTTCAAGATCCGCCACAACATCGAGGACGGCAGCGTGCAGCTCGCCGACCACTACCAGCAGAACACC
GTCTTCTTGCCGTAGTTCCACTTGAAGTTCTAGGCGGTGTTGTAGCTCCTGCCGTCGCACGTCGAGCGGCTGGTGATGGTCGTCTTGTGG
GlnLysAsnGlyIleLysValAsnPheLysIleArgHisAsnIleGluAspGlySerValGlnLeuAlaAspHisTyrGlnGlnAsnThr

CCCATCGGCGACGGCCCCGTGCTGCTGCCCGACAACCACTACCTGAGCACCCAGTCCGCCCTGAGCAAAGACCCCAACGAGAAGCGCGAT
GGGTAGCCGCTGCCGGGGCACGACGACGGGCTGTTGGTGATGGACTCGTGGGTCAGGCGGGACTCGTTTCTGGGGTTGCTCTTCGCGCTA
ProIleGlyAspGlyProValLeuLeuProAspAsnHisTyrLeuSerThrGlnSerAlaLeuSerLysAspProAsnGluLysArgAsp

CACATGGTCCTGCTGGAGTTCGTGACCGCCGCCGGGATCACTCTCGGCATGGACGAGCTGTACAAGTCCTCTAGAAACAGCGATGGTGAG
GTGTACCAGGACGACCTCAAGCACTGGCGGCGGCCCTAGTGAGAGCCGTACCTGCTCGACATGTTCAGGAGATCTTTGTCGCTACCACTC
HisMetValLeuLeuGluPheValThrAlaAlaGlyIleThrLeuGlyMetAspGluLeuTyrLysSerSerArgAsnSerAspGlyGlu

AAGGCCACCAAAGTGCAGGACATCAAAAACAACCTGAAGGAGGCCATTGAAACCATTGTGGCCGCCATGAGCAACCTGGTGCCCCCCGTG
TTCCGGTGGTTTCACGTCCTGTAGTTTTTGTTGGACTTCCTCCGGTAACTTTGGTAACACCGGCGGTACTCGTTGGACCACGGGGGGCAC
LysAlaThrLysValGlnAspIleLysAsnAsnLeuLysGluAlaIleGluThrIleValAlaAlaMetSerAsnLeuValProProVal

GAGCTGGCCAACCCTGAGAACCAGTTCAGAGTGGACTACATTCTGAGCGTGATGAACGTGCCAAACTTTGACTTCCCACCTGAATTCTAT
CTCGACCGGTTGGGACTCTTGGTCAAGTCTCACCTGATGTAAGACTCGCACTACTTGCACGGTTTGAAACTGAAGGGTGGACTTAAGATA
GluLeuAlaAsnProGluAsnGlnPheArgValAspTyrIleLeuSerValMetAsnValProAsnPheAspPheProProGluPheTyr

GAGCATGCCAAGGCTCTGTGGGAGGATGAGGGAGTTCGTGCCTGCTACGAGCGCTCCAACGAGTACCAGCTGATCGACTGTGCCCAGTAC
CTCGTACGGTTCCGAGACACCCTCCTACTCCCTCAAGCACGGACGATGCTCGCGAGGTTGCTCATGGTCGACTAGCTGACACGGGTCATG
GluHisAlaLysAlaLeuTrpGluAspGluGlyValArgAlaCysTyrGluArgSerAsnGluTyrGlnLeuIleAspCysAlaGlnTyr

TTCCTGGACAAGATTGATGTGATCAAGCAGGCCGACTACGTGCCAAGTGACCAGGACCTGCTTCGCTGCCGCGTCCTGACCTCTGGAATC
AAGGACCTGTTCTAACTACACTAGTTCGTCCGGCTGATGCACGGTTCACTGGTCCTGGACGAAGCGACGGCGCAGGACTGGAGACCTTAG
PheLeuAspLysIleAspValIleLysGlnAlaAspTyrValProSerAspGlnAspLeuLeuArgCysArgValLeuThrSerGlyIle

FIG.9C

TTTGAGACCAAGTTCCAGGTGGACAAAGTCAACTTCCACATGTTCGATGTGGGCGGCCAGCGCGATGAACGCCGCAAGTGGATCCAGTGC
AAACTCTGGTTCAAGGTCCACCTGTTTCAGTTGAAGGTGTACAAGCTACACCCGCCGGTCGCGCTACTTGCGGCGTTCACCTAGGTCACG
PheGluThrLysPheGlnValAspLysValAsnPheHisMetPheAspValGlyGlyGlnArgAspGluArgArgLysTrpIleGlnCys

TTCAATGATGTGACTGCCATCATCTTCGTGGTGGCCAGCAGCAGCTACAACATGGTCATCCGGGAGGACAACCAGACCAACCGTCTGCAG
AAGTTACTACACTGACGGTAGTAGAAGCACCACCGGTCGTCGTCGATGTTGTACCAGTAGGCCCTCCTGTTGGTCTGGTTGGCAGACGTC
PheAsnAspValThrAlaIleIlePheValValAlaSerSerSerTyrAsnMetValIleArgGluAspAsnGlnThrAsnArgLeuGln

GAGGCTCTGAACCTCTTCAAGAGCATCTGGAACAACAGATGGCTGCGTACCATCTCTGTGATCCTCTTCCTCAACAAGCAAGATCTGCTT
CTCCGAGACTTGGAGAAGTTCTCGTAGACCTTGTTGTCTACCGACGCATGGTAGAGACACTAGGAGAAGGAGTTGTTCGTTCTAGACGAA
GluAlaLeuAsnLeuPheLysSerIleTrpAsnAsnArgTrpLeuArgThrIleSerValIleLeuPheLeuAsnLysGlnAspLeuLeu

GCTGAGAAGGTCCTCGCTGGGAAATCGAAGATTGAGGACTACTTTCCAGAGTTCGCTCGCTACACCACTCCTGAGGATGCGACTCCCGAG
CGACTCTTCCAGGAGCGACCCTTTAGCTTCTAACTCCTGATGAAAGGTCTCAAGCGAGCGATGTGGTGAGGACTCCTACGCTGAGGGCTC
AlaGluLysValLeuAlaGlyLysSerLysIleGluAspTyrPheProGluPheAlaArgTyrThrThrProGluAspAlaThrProGlu

CCCGGAGAGGACCCACGCGTGACCCGGGCCAAGTACTTCATCCGGGATGAGTTTCTGAGAATCAGCACTGCTAGTGGAGATGGACGTCAC
GGGCCTCTCCTGGGTGCGCACTGGGCCCGGTTCATGAAGTAGGCCCTACTCAAAGACTCTTAGTCGTGACGATCACCTCTACCTGCAGTG
ProGlyGluAspProArgValThrArgAlaLysTyrPheIleArgAspGluPheLeuArgIleSerThrAlaSerGlyAspGlyArgHis

TACTGCTACCCTCACTTTACCTGCGCCGTGGACACTGAGAACATCCGCCGTGTCTTCAACGACTGCCGTGACATCATCCAGCGCATGCAT
ATGACGATGGGAGTGAAATGGACGCGGCACCTGTGACTCTTGTAGGCGGCACAGAAGTTGCTGACGGCACTGTAGTAGGTCGCGTACGTA
TyrCysTyrProHisPheThrCysAlaValAspThrGluAsnIleArgArgValPheAsnAspCysArgAspIleIleGlnArgMetHis

CTTCGCCAATACGAGCTGCTCTAAGAAGGGAACGCCCAAATTTAATTCAGCCTTAAGCACAATTAATTAAGAGTGAAACGCAATCGTACA
GAAGCGGTTATGCTCGACGAGATTCTTCCCTTGCGGGTTTAAATTAAGTCGGAATTCGTGTTAATTAATTCTCACTTTGCGTTAGCATGT
LeuArgGlnTyrGluLeuLeuter AGCAGTTGATCACCCACCATAGGGCATGATCAACACCGCAACCTTTCCCTTTTCTCCCCAGTGATTCTGAAAACCCCCTCTTCCCTTCAG
TCGTCAACTAGTGGGTGGTATCCCGTACTAGTTGTGGCGTTGGAAAGGGAAAAGAGGGGTCACTAAGACTTTTGGGGGAGAAGGGAAGTC

CTTGCTTAGATGTTCTCTAGA    2091
GAACGAATCTACAAGAGATCT

GFP FUSION PROTEINS AND THEIR USE

This application is a national stage application of PCT/US02/21484 filed Jul. 3, 2002, which claims priority to U.S. Ser. No. 60/303,622 filed Jul. 6, 2001.

This invention was made with government support under MH39595-10, AG15482 and awarded by the National Institute of Health (NIH). The Government has certain rights in the invention.

The present invention relates a protein that is constructed by adding a green fluorescent protein designated GFP that is internal to the amino acid sequence of a G protein, in particular the Gαs protein. The resulting fusion protein is a non-radioactive marker used, for example, for high throughput screening of G protein-coupled receptor drug targets.

BACKGROUND OF THE INVENTION

A family of heterotrimeric nucleotide-binding proteins that bind to guanine (G proteins) transduces chemical and sensory signals across the plasma membrane by sequential interactions with receptor and second messenger-generating effectors. Because of the wide array of cellular processes that are mediated by G proteins, the study of G protein function and regulation is a significant area of research in the signal transduction field. There are reports containing suggestions of an important function for G protein at cellular locations other than the plasma membrane. Certain G proteins were detected at intracellular membranes, for example, the Golgi complex, whereas others associate with cytoskeletal structures, for example, microtubules and microfilaments. The mechanisms that govern the cellular destinations of G proteins and the relative proportions of G proteins that traffic to subcellular compartment are just beginning to be revealed.

G proteins are reported to couple the receptors for hormones or neurotransmitters to intracellular effectors such as adenylyl cyclase or phospholipase C. Twenty forms of the α-subunit of G proteins were identified and each is involved in the conveyance of multiple hormonal neurotransmitter signals from the outside of the cell to the effects that those hormones and neurotransmitters have on the inside of the cell.

G proteins may leave the membrane in response to neurotransmitter or hormone signals, but this has been very difficult to prove.

GFP, an autofluorescent protein of 238 amino acids, is a reporter molecule useful to monitor gene and protein expression and to observe the dynamics of protein movements within the living cell. Fusing GFP to another protein of interest allows time-course studies to be performed on living samples in real time. Accounts of GFP fusion proteins include receptors, secretory proteins, cytoskeleton proteins and signaling molecules. Presently, GFP fusion proteins are constructed by generating an expression construct that contains GFP fused in frame to either the N-amino or C-carboxyl terminus of the protein of interest. However, this attachment may alter the function of the protein fused with GFP consequently may not give results reflective of the natural state.

SUMMARY OF THE INVENTION

Fusion of a GFP protein at either $NH_2$ or COOH ends of Gαs protein subunits is not acceptable because the $NH_2$ region is important for association with Gαs protein βγ subunits, and the COOH terminal is required for interaction with receptors. Consequently, a biologically active Gαs-GFP that incorporated GFP at some other positions of the molecule was developed. Suitable regions for insertion of a GFP sequence are those regions that are free of interactions with receptors or effectors.

A fusion protein was constructed by inserting an amino acid sequence of a green fluorescent protein designated GFP, into the interior of an amino acid sequence of a G-protein, in particular the Gαs protein. Although, green fluorescent proteins have been inserted at either end of G-proteins, a method was needed to insert GFP into the internal amino acid sequence of a G-protein without altering the biological activity of the protein.

Green fluorescent protein (GFP) was inserted within the internal amino acid sequence of Gαs to generate a Gαs-GFP fusion protein. The fusion protein maintained a bright green fluorescence and was also identified by antibodies against Gαs or GFP, respectively. The cellular distribution of Gαs-GFP was similar to that of endogenous Gαs. Gαs-GFP was tightly coupled to the β adrenergic receptor to activate the Gαs effector, adenylyl cyclase. Activation of Gαs-GFP by cholera toxin caused a gradual displacement of Gαs-GFP from the plasma membrane throughout the cytoplasm in living cells. Unlike the slow release of Gαs-GFP induced by cholera toxin, the β adrenergic agonist isoproterenol caused a rapid partial release of Gαs-GFP into the cytoplasm. At 1 min after treatment with isoproterenol, the extent of this Gαs-GFP release from plasma membrane was maximal. Translocation of Gαs-GFP induced by isoproterenol suggested that the internalization of Gαs might play a role in signal transduction by interacting with effector molecules and cytoskeletal elements at multiple cellular sites.

Uses for the Gαs-GFP fusion construct of the present invention include:

1. G proteins from the intracellular plasma membrane move in response to activation by an antagonist. Following the activation of a G protein and discovering the time course for that activation. The occupancy of a receptor by an agonist is only the first step in a signaling cascade. The intracellular processes might be activated at different rates or, at specific areas within a cell. Gαs-GFP is useful because it can be followed in real time as events take place without disrupting natural progress of events.

2. Tracking protein functions in living cells.

3. As a non-radioactive marker for high throughput screening of G-proteins coupled receptor drug targets, following the course of activation of a putative receptor or a putative ligand. For example, if a drug company has a candidate that it believes activates G protein coupled receptors in a functional sense, the Gαs-GFP fusion construct is useful as a high throughput screen, because a change in fluorescence in response to the application of an agonist is detectable. Conversely, the activity of an antagonist is visualized by adding it in 96 well plates, and screening significant numbers of samples on a fluorimeter to determine which compounds block the expected fluorescence change. Gαs-GFP could be used in combination with a fluorescent receptor such as that developed by the Biosignal Corporation in Montreal. To do this, cells are transfected with fluorescent receptors and Gαs-GFP. A ligand which activated the receptor in such a way that the G protein was also activated should decrease the fluorescence of GFP induced by the emitted light from the receptor (fluorescence resonance energy transfer-FRET). Thus, a number of candidate compounds may be screened for receptor and G protein activation by conducting these assays in e.g. 96 well plates.

4. The use of green fluorescent protein (GFP) in the study of cellular signaling allows not only the observation of G protein trafficking, but the opportunity to study the dynamics of G proteins in real time as well as their function.

Other molecules may be modified in the same way, for example the other of the 20 G protein α subunits. Insertion sites for GFP are determined by an analysis of the sequence. None of the Gαs can be modified by adding GFP to either the amino or carboxy terminus because their function would be destroyed. Putting the GFP in the internal regions does not harm the effects of the protein, but rather bestows on its new properties. Several other signaling molecules may be suitable candidates for the fusion proteins of the present invention.

5. Gαs-GFP is modified in such a way that it will couple to other receptors. Modification of amino acids near the carboxy terminal generates a fluorescent Γα that is capable of coupling to receptors which normally couple to Gαi, Gαo or Gαq (Conklin, et al., 1996). This will allow the same fluorescent G protein to assess potency and efficacy of putative agonists and agonists for a large number of G protein coupled receptors.

The 5 C terminal residues of Gαs are QYELL (SEQ ID NO: 3). They are replaced with DCGLF (SEQ ID NO: 4) for Gi1 or Gi2, with ECGLY (SEQ ID NO: 5) for Gi3, with RCGLY (SEQ ID NO: 6) for Go, and with EYNLV (SEQ ID NO: 7) for Gq.

COS1 or HEK293 cells are suitable because they are easy to transfect. These or comparable cells are co-transfected with GFP-Gαs (either in its native form or engineered to couple to a receptor which normally couples to Gi or Gq) and the desired receptor. Putative agonists are screened by monitoring loss of fluorescence from the membrane. High-throughput fluorescence monitoring instruments that are known to those of skill in the art are used for this purpose. Putative antagonists are screened by assessing their ability to block the effects of known receptor agonists to evoke this phenomenon.

BRIEF DESCRIPTION OF THE DRAWINGS

FIG. 9A-9C are cDNA (nucleotide) (SEQ ID NO: 1) and its complement and amino acid sequences (SEQ ID NO: 2) of the Gαs-GFP. The letters in a box indicate the start codon for Gαs-GFP. The circled letters form the stop codon for Gαs-GFP. A, G, T and C are abbreviations of Adenine, Guanine, Thymine and Cytosine, respectively.

DETAILED DESCRIPTION OF THE INVENTION

Construction of Gαs-GFP

Figure 1:
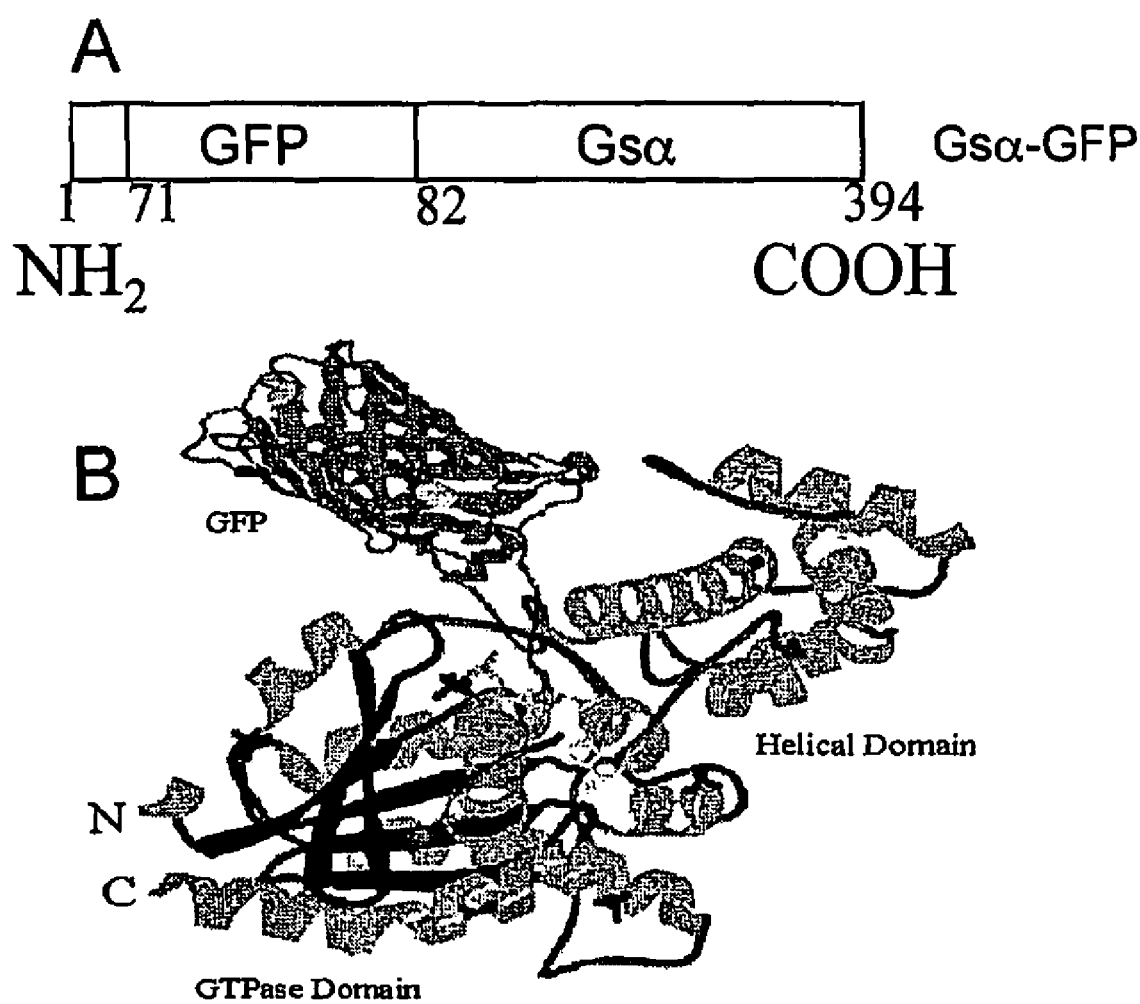
FIG. 1 shows Gαs fusion protein cDNA construction. (A) shows a schematic of Gαs-GFP. Gαs-GFP defines the fusion protein in which GFP was inserted within the $NH_2$-terminal domain of the long Gαs. (B) presents a model of Gαs-GFP. The structure of GFP is shaded. The Gαs subunit structure is that of Gαs-GTPγS.

Full length cDNAs encoding Gαs were excised from the PcDNA-1 vector by digesting with Sam I and Xba I restriction enzymes. The full length EGFP cDNA was obtained by PCR from the PEGFP-N3 using appropriate primers (sense 5' GGAATTCATGAGCAAGGGCGAGGAACTG-3' (SEQ ID NO: 8); antisense 5'-GCTCTAGACGACTTGTA-CAGCTCGT-3') (SEQ ID NO: 9) and adding restriction sites to its cDNA (EcoR I at the initiation codon and Xba I at end of cDNA). To insert the EGFP within the sequence of Gαs, the first fragment of Gαs (from 1 to 71 amino acids) was amplified by PCR with restriction sites for Kap 1 at initiation codon and EcoR I at end of the fragment. The cDNA of the fragment was cloned into PcDNA3 vector by the Kap 1 and EcoR 1 restriction sites using primers (sense 5'GGGTAC-CATGGGCTGCCTCGGCAACA-3' (SEQ ID NO: 10); antisense 5'-GGAATTCGTCCTCTTCGCCGCCCTTCT-3') (SEQ ID NO: 11). Modified 7 EGFP cDNA was spliced into the first fragment of Gαs by EcoR 1 and Xba 1 restriction sites on PcDNA3 to get the fusion cDNA sequence of the first fragment of Gαs and EGFP. The second fragment of Gαs (from 82 to 394 amino acids) was also obtained using PCR with appropriate primers. The sense primer contained a part of a sequence overlapping with the 3' end of EGFP (5'-CA-GAGCTGGACAAGTCCAACAGCGATGGTGAGAA-3') (SEQ ID NO: 12). The anti-sense primer contained an additional Xba 1 restriction site (5'-GCTCTAGACGACTTGTA-CAGCTCGT-3') (SEQ ID NO: 9) The presenion cDNA fragment described above was amplified by PCR. The Gαs-GFP fusion fragment and the second fragment of Gαs were also linked using PCR strategy. The full length Gαs-GFP was cloned into PcDNA3 at Kap 1 and Xba 1 restriction sites. All DNA manipulations, including ligations, PCR, bacterial transformation were carried out using procedures disclosed herein. Plasmid purification was done using "plasmid purification kit" following the manufacture instruction (QIAGEN).

Ligation Protocol

1. In a 1.5 ml microfuge tube, cut 10 mL expression vector with the desired restricted enzyme in a total volume of 20 mL for 2 h at 31° C.
2. Loading the sample into 1% agarose gel, run the gel applying a voltage of 100 V. Run the gel long enough to resolve the fragments of interest.
3. Turn off the power supply and remove the gel from the apparatus.
4. Using "Gel Extraction Kit" (QIAGEN), purify fragments from gel.
5. In 0.5 ml microfuge tube, mix the fragments of vector (0.03 mg) and relevant inserts, add 5 mL 4' ligation buffer (GIB-COBRL), incubating in a total volume of 20 mL at 14° C. overnight with 0.1 units $T_4$ ligase.
6. Take out 10 mL to transformation.

Polymerase Chain Reaction

1. In 0.5 ml thin wall tube mix the following ingredients.

| | |
|---|---|
| 10' buffer (GIBCOBRL) | 5 μL |
| $MgCl_2$ (GIBCOBRL) | 5 μL |
| primer 1 | 1 μL |
| primer 2 | 1 μL |
| template DNA | 0.5 μL |
| 4 dNTP mix (GIBCOBRL) | 10 μL |
| $H_2O$ | 26.5 μL |
| Taq polymerase (GIBCOBRL) | 1 μL |
| | 50 mL |

2. Spin down one time for 15 seconds and put one-drop mineral oil in tube.
3. Turn on the automated thermal cycler.
4. First denature simples 2 min at 94° C., then run program for 35 cycles.
 Denature 90 seconds
 Anneal 50 seconds at 58° C.
 Extend 1 min at 72° C.
When cycles finish, 7 min perform extra-extend at 72° C.
5. Run gel and purify the DNA with "PCP Purification Kit" (QIAGEN).

Transformation Protocol

1. Add 5 ml of LB medium (10 g tryptone, 5 g yeast extract, 10 g NaCl in 1 L $H_2O$) to sterile 10 ml tube.
2. Scrape HB 101 bacterial cells (one colony) from stock plate with loop. Transfer cells to medium and shake bacterial cells off loop. Put the tube in shaking incubator at 31° C. for 12 h.
3. Spin down bacterial cells at 2000×g for 3 min at room temperature.
4. Gently resuspend pellet of bacterial cells in 1 ml 50 mM $CaCl^2$, incubate for 40 min on ice.
5. Spin down again at 2000×g for 3 min at 4° C. Resuspend pellet of bacterial cells in 100 ml 50 mM $CaCl^2$.
6. In 1.5 ml sterile microfuge tube, add 10 mL ligated plasmid vector, then mix it with 100 mL competent bacterial cells.
7. Incubate the mixture on ice for 20 min and then transfer tube to 42° C. for heat shock for 30 seconds.
8. Take the mixture, and add to plate (with antibiotic), agar side top incubating at 37° C. overnight.

Figure 2:
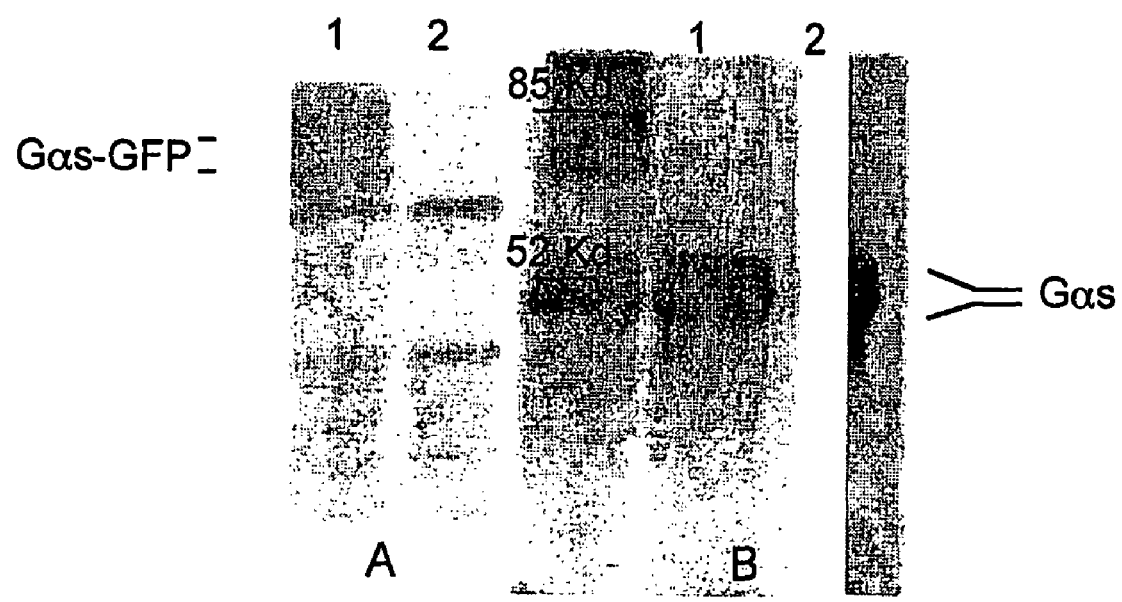
FIG. 2 shows expression of the Gαs-GFP fusion in COS-1 cells. COS-1 cells were lysed 24 h after transiently transfecting with Gαs-GFP (3 μg DNA). 30 μg protein was loaded, separated by SDS-PAGE gel, detected with polyclonal antibody against Gαs (panel B) or monoclonal antibody against GFP (Panel A), as indicated. Lane 1 represents a lysate from cells transfected with Gαs-GFP, Lane 2 is the lysate from control cells.

Three Gαs-GFP fusion constructs were made and expressed in COS-1 cells. In the Gαs-NGFP expression vector, in which the GFP was spliced to the N-amino terminus of Gαs sequence, the fusion protein could not associate with the plasma membrane of cells (see FIG. 1, FIG. 2A). The attachment of palmitate at Cys-3 of Gαs is required both for its membrane association and for its ability to mediate hormonal stimulation of adenylyl cyclase. A sequence motif that serves as a predictor for a subset of palmitoylated proteins is Met-Gly-Cys at the amino terminus of a protein. This motif found in the Gi and Gαs subfamily of G-protein subunits and other proteins such as receptor tyrosine kinases. The GFP connected with the amino terminus of Gαs may affect the palmitoylation of Cys-3. A GFP tagged COOH terminal of Gαs, Gαs-CGFP was also constructed. Although this attached to the membrane, it did not respond to hormone activation.

Gαs exists as a short and a long splice variant. Compared with short Gαs, long Gαs contains an additional 15 amino acids inserted at position 72 of the polypeptide chain, and there is an exchange of glutamate for apartate at position 71. Although there has been some indication that subtle differences between short Gαs and long Gαs exist, the general function of the two forms is similar. No substantial difference in the function of the two forms has been detected. Furthermore, the yeast Gαs, GPA1, has an "extra loop" in this region as well. Levis et al. (1992) modified the long Gαs form at a site (residues 77-81) within the 15 amino acid insert to confer upon it recognition by an antibody directed against a well-defined peptide of the influenza hemaglutinin (HA). Addition of the HA epitope did not alter the ability of wild type Gαs to mediate hormonal stimulation of adenylyl cyclase or to attach to cell membranes. Given the possibility that this region was "inert", a Gαs-GFP2 fusion protein was constructed by replacing the residues (72-81) within the long Gαs with a GFP sequence (see FIG. 1). A western blot of membrane and cytosolic fractions (FIG. 2B), probed with an anti-Gαs polyclonal or anti-GFP monoclonal antibody, shows that Gαs-GFP2 is expressed in COS-1 cells with a distribution comparable to that of intrinsic Gαs. These results indicate that the GFP in the Gαs-GFP2 should not alter the attachment of Gαs to membranes. In addition, the fluorescence of GFP in Gαs-GFP2 is visual and stable with UV irradiation.

Figure 3:
FIG. 3 shows Gαs-GFP is associated with the plasma membrane in transfected cells. 24 h post-transfection, cells were observed by confocal microscopy at 37° C. A computer-generated cross section of a typical cell is displayed on the top (x-z plane) and on the right (y-z plane). Each image shown is representative of at least 20 cells subjected to a z-scan analysis. Similar results were obtained with COS-1, PC12, and HEK 293 cells.
Figure 3:
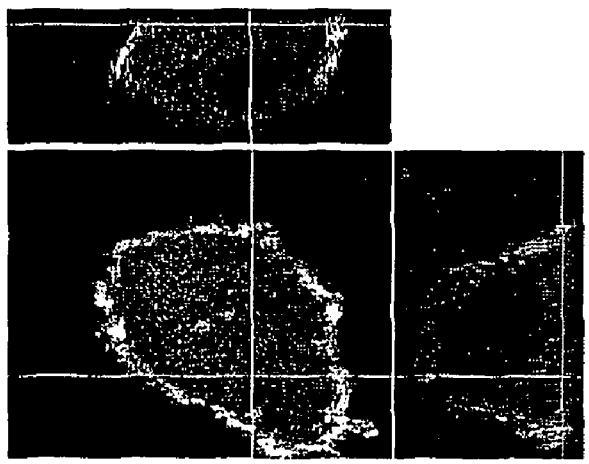
Figure 3:

Based on the α-carbon model of the α-subunit of the retinal G-protein transducin, the sequence within which the 15 amino acid insert is localized in the long Gαs serves as a linker between the ras-like domain and the α-helical domain. The guanine nucleotide-binding site is embedded between these two domains. Thus, the change in this linker sequence might be expected to diminish the ability of binding to guanine nucleotides of Gαs. To study this, COS-1 cells were co-transfected with Gαs-GFP2 and β-adrenergic receptor cDNA. COS1 membranes were incubated with the photoaffinity GTP analog $^{32}$P AAGTP as in the presence and absence of a beta adrenergic agonist. Labeling of membranes from the transfected COS-1 cells was accomplished by incubating with 0.1 mM [$^{32}$P] AAGTP for 5 min at 23° C., followed by treatment with isoproterenol (ISO) for 3 min. Gαs-GFP2 in COS-1 bound [$^{32}$P] AAGTP in response to ISO (FIG. 3). This result dramatically and unexpectedly demonstrated that the insertion of GFP into the linker sequence between two domains of Gαs does not disrupt agonist-induced guanine nucleotide exchange.

Figure 4:
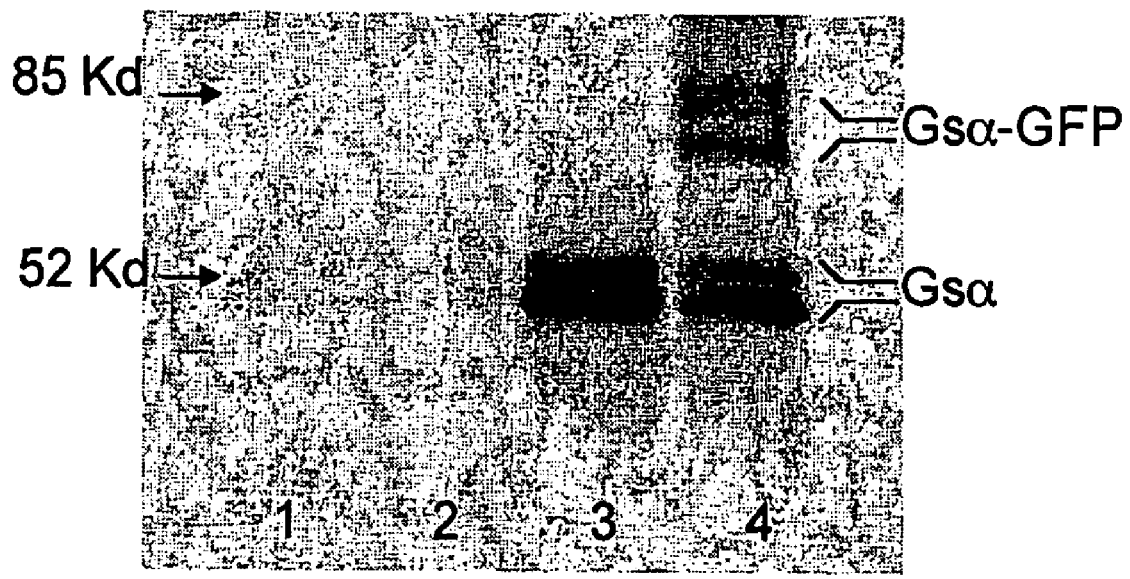
FIG. 4 shows subcellular distribution of Gαs-GFP in COS-1 cells. Particulate and soluble fractions were isolated from cells transfected with Gαs-GFP constructs 24 h post transfection as described herein. 20 μg protein was loaded, separated by SDS-PAGE gel and detected with a polyclonal antibody against the C-terminal peptide of Gαs. Lanes 1 and 2 represent the soluble portion from the control cells or cells transfected with Gαs-GFP, respectively. Lanes 3 and 4 indicate the particulate fraction from control cells or cells transfected with Gαs-GFP, respectively.
Figure 5:
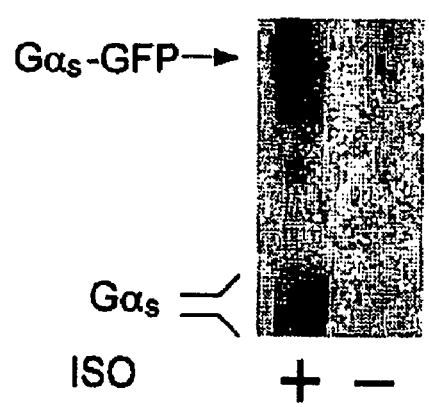
FIG. 5 shows Gαs-GFP binding to AAGTP. COS-1 cells were co-transfected with cDNA encoding Gαs-GFP (1 μg) and β-adrenergic receptor (4 μg). (A) Shows cell membranes prepared 24 h post-transfection and incubated with $^{32}P$ AAGTP in the presence and absence of isoproterenol (as indicated). Proteins were resolved by SDS-PAGE and autoradiography. Results shown are from one of four similar experiments. (B) Presents densitometric analysis of Gαs-GFP binding to AAGTP. Densitometric analysis of four independent experiments were carried out and displayed in densitometric units. [Shown is the mean±Standard error, n=4, ** indicates significant difference from control treated without ISO ($P<0.01$].
Figure 5:
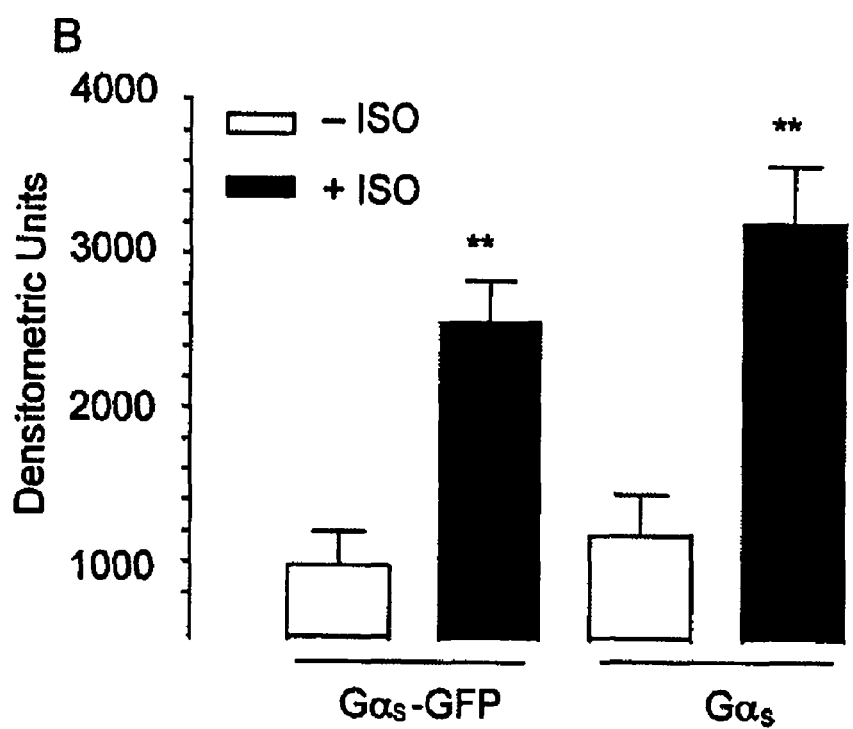

Cholera toxin activates Gαs by directly ADP ribosylating arginine 201 of Gαs and inhibiting the intrinsic GTPase. Thus, cholera toxin locks Gαs in the activated state. After, cholera toxin-activated was no longer observed at the plasma membrane, but instead it was distributed throughout the cytoplasm. Increased solubility of Gαs may correlate with activation-induced depalmitoylation of Gαs, but it is not absolutely clear that the removal of the lipid group is necessary for cytosolic translocation. FIG. 4 shows that the Gαs-GFP on the cellular membrane is internalized gradually subsequent to treatment of cells with cholera toxin. Cholera toxin activation of Gαs-GFP also provides further evidence that the fusion protein is capable of normal pysiological function.

The physiologic consequences of β-adrenergic receptor activation of Gαs were observed by examining the response of Gαs-GFP cos1 cells to isoproterenol. The rapid translocation of Gαs from membrane to cytoplasm was clearly delineated.

Figure 6:
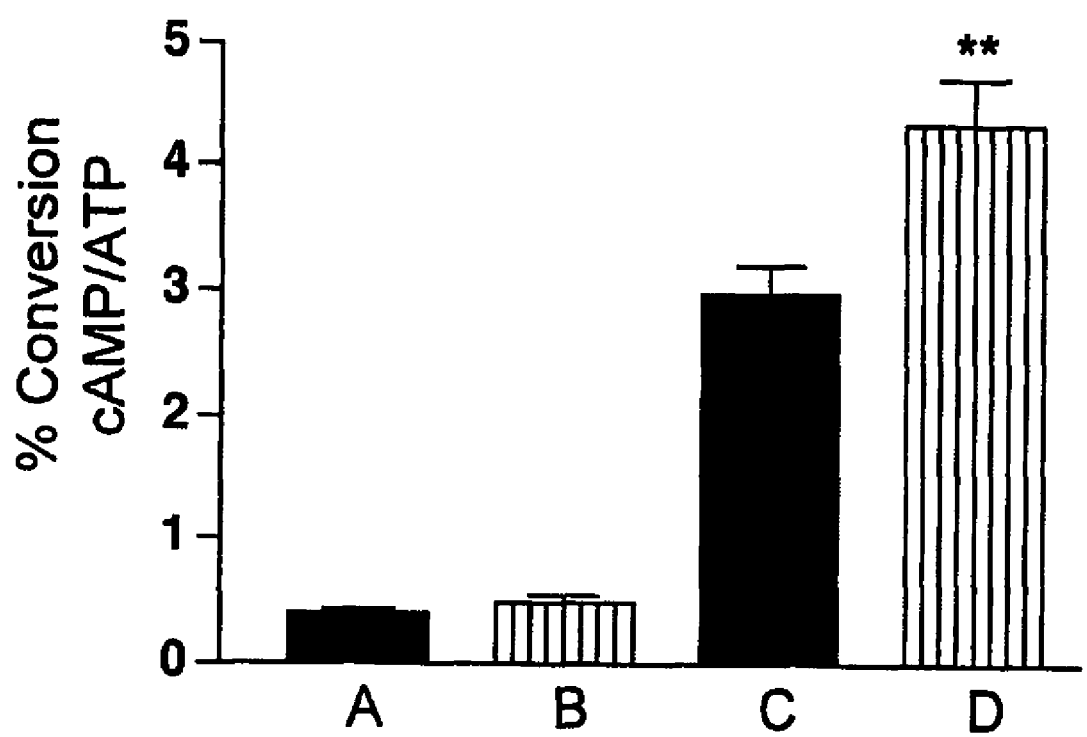
FIG. 6 shows Gαs-GFP activates adenylyl cyclase. Cells were transfected with GFP (control) or Gαs-GFP, respectively and assayed for cAMP formation in the presence or absence of isoproterenol (ISO: 50 μM) as indicated. (A) control cells in the absence of ISO. (B) Gαs-GFP transfected cells in the absence of ISO. C. control cells with ISO. D. Gαs-GFP transfected cells treated with ISO. The values shown are mean±standard error of nine samples from three experiments. Identical levels of Gαs-GFP in each group were determined by western blotting. ** indicates significant difference from control cells treated without ISO; ($P<0.01$).
Figure 7:
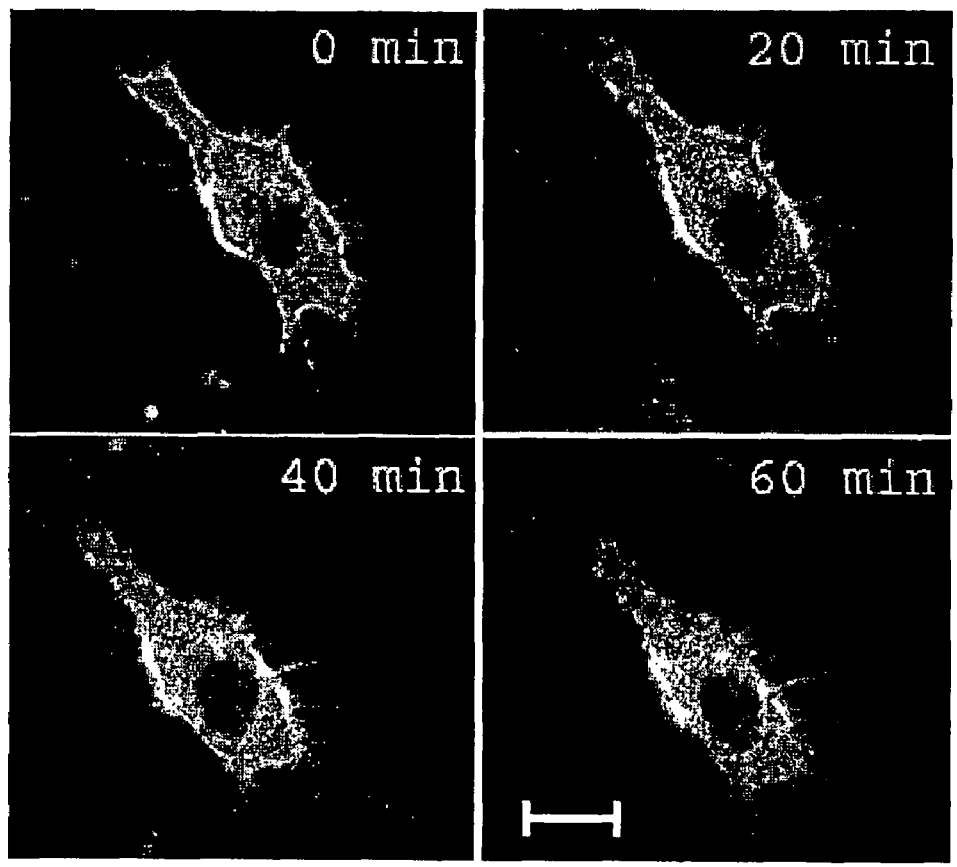
FIG. 7 demonstrates cholera toxin treatment translocates Gαs-GFP in living PC12 cells. (A) 24 h post-transfection with Gαs-GFP, media was replaced as described in Methods and living cells were viewed by confocal microscopy at 37° C. Cells were initially imaged (0 min), cholera toxin (3 μg/ml) was added and cells were observed for 1 h. Bar=10 μm. (B) computer-generated cross section of the whole cell after completion of the one hour, is displayed on the top (x-z plane) and on the right (y-z plane). Results shown are from one of four comparable experiments. Observation of other cell lines (COS-1 and HEK 293) showed similar results for response to cholera toxin.
Figure 7:
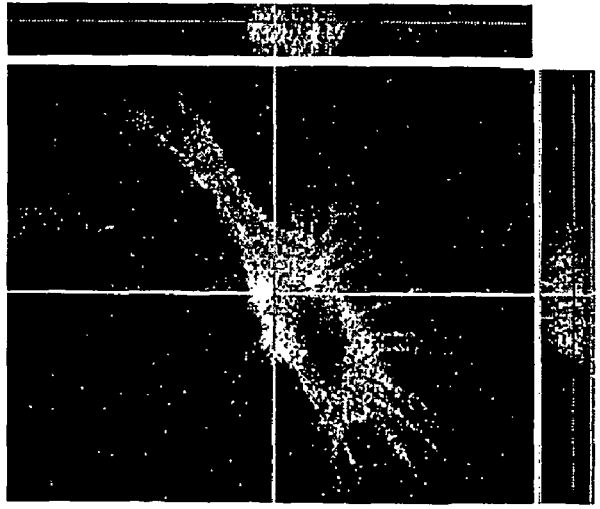
Figure 8:
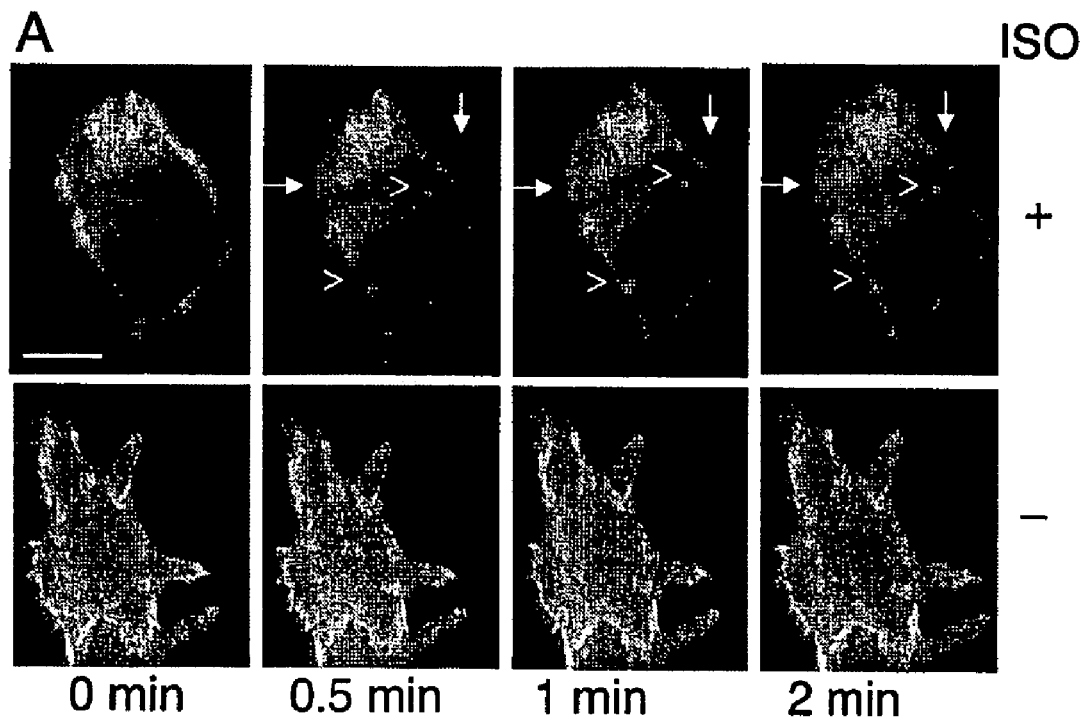
FIG. 8 shows isoproterenol-stimulated rapid internalization of Gαs-GFP in living COS cells. Cells were transfected with Gαs-GFP and observed 24 h later at 37° C. with confocal or digital fluorescent microscopy. (A) cells were treated with or without isoproterenol (20 μM), and images were captured every 5 seconds (A video scan; showed COS-1 cell treatment with ISO for 2 min. and; shown control COS-1 cell for 2 min). Arrows indicate areas where membrane-bound Gαs-GFP released from plasma membrane significantly. Clusters of Gαs-GFP form subjacent to the plasma membrane (indicates by open arrowhead). (B) Observation of Gαs-GFP release from plasma membrane using confocal microscopy. Arrows display regions where Gαs-GFP released from plasma membrane significantly. The arrowheads indicate the sites where the Gαs-GFP was inserted after the 2 minutes time point. Bar=10 mm. These results are typical of 40 of 58 cells observed during the course of 15 experiments. Approximately 70% of the cells showed internalized Gαs-GFP in response to isoproterenol [ISO]. Thirty percent did not show a significant response to this agonist.
Figure 8:
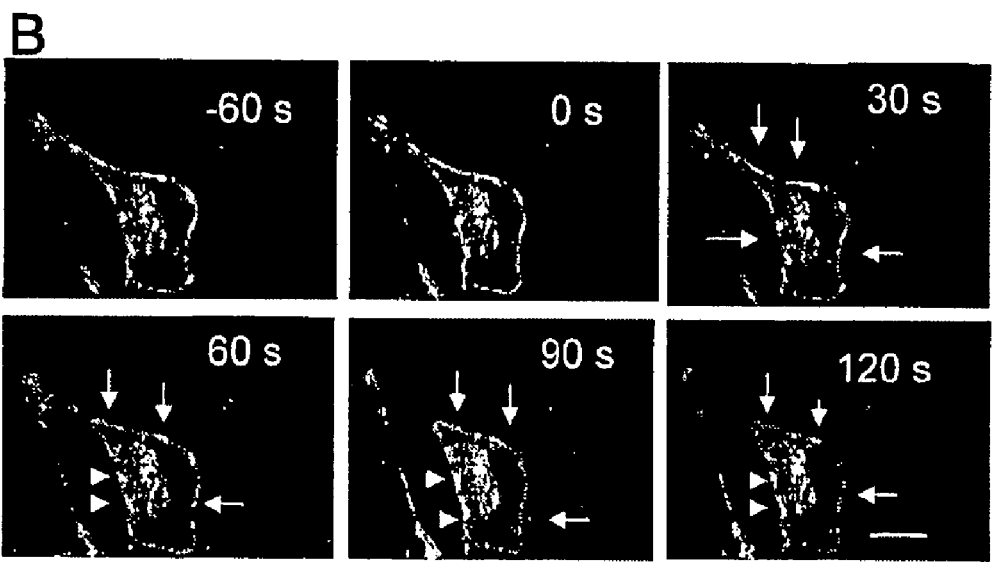

To determine whether Gαs-GFP was fully physiologically active, tests were performed to see if the fusion protein was capable of activating adenylyl cyclase. By measurement of cAMP accumulation in COS-1 cells transfected in different conditions, the overexpression of Gαs-GFP was found not to alter the base level of cAMP in cells. Isoproterenol treated cells showed the cAMP production in Gαs-GFP cells to be significantly higher than cells transfected with GFP-vector alone (FIG. 6).

Thus, assay of subcellular distribution and signaling function shows in vitro and in vivo that the GFP insertion into the Gαs amino acid sequence does not substantially affect normal function of Gαs. The study indicates a new approach to constructing GFP fusion protein and the study of G protein molecular signaling transduction in cells.

DOCUMENTS CITED

Conklin, B. R., Herzmark, P., Ishida, S., Voyno-Yasenetskaya, T. A., Sun, Y., Farfel, Z. and Bourne, H. R. (1996) Carboxyl-terminal mutations of Gq alpha and Gs alpha that alter the fidelity of receptor activation. *Mol. Pharmacol.* 50: 885-890.

Hugges, T. E., Zhang, H., Logothetis, D. E., Berlot, C. H. (2001) Visualization of a functional Gαq-green fluorescent protein fusion in living cells. *J. Biol. Chem.* 276: 4227-4235.

Kallal, L. and Benovic, J. L. (2000) Using green fluorescent proteins to study G-protein receptor localization and trafficking. *TiPS* 21: 175-180.

Levis, M. J. and Bourne, H. R. (1992) Activation of a subunit of Gαs in intact cells alters its abundance, rate of degradation, and membrane avidity. *J. Cell Bio.* 5:1297-1300.

Sunahara, R. K., Tesmer J. J. G., Gilman, A. G. and Sprang S. R. (1997) Crystal structure of the adenylyl cyclase activator Gαs. *Science* 278: 1943-1947.

We claim:

1. A fusion protein comprising a green fluorescent protein inserted between the GTPase and the helical domain of $G\alpha_S$, wherein the $G\alpha_S$ activates adenylyl cyclase and the fusion protein translocates from the plasma membrane into the cytoplasm upon activation.

2. The fusion protein of claim 1, wherein the insertion is at regions that are free of interactions with receptors or effectors.

3. The fusion protein of claim 1 modified for specific receptors by replacing amino acid residues at the C terminal end of $G\alpha_s$.

4. A method for making a fusion protein, said method comprising:
   (a) obtaining a molecule having the amino acid sequence of a green fluorescent protein; and
   (b) inserting the molecule between the GTPase and the helical domain of $G\alpha_S$.

5. The method of claim 4 wherein the fusion protein has the amino acid sequence of SEQ ID NO: 2.

6. A method to follow an activation of a G-protein receptor by a candidate drug said method comprising:
   (a) obtaining a $G\alpha_s$ green fluorescent fusion protein, wherein the green fluorescent protein is inserted between the GTPase and the helical domain of $G\alpha_S$;
   (b) monitoring fluorescence of the fusion protein in response to the candidate drug;
   (c) inferring from a change in membrane fluorescence whether the drug is an agonist or antagonist; and
   (d) following the activation of the G-protein receptor by the candidate drug.

7. The fusion protein of claim 1 comprising the amino acid sequence of SEQ ID NO: 2.

8. The fusion protein of claim 1, wherein the fusion protein internalizes.

* * * * *

SEQUENCE LISTING

```
<160> NUMBER OF SEQ ID NOS: 12

<210> SEQ ID NO 1
<211> LENGTH: 2091
<212> TYPE: DNA
<213> ORGANISM: Artificial Sequence
<220> FEATURE:
<221> NAME/KEY: CDS
<222> LOCATION: (10)..(1911)
<220> FEATURE:
<223> OTHER INFORMATION: Description of Artificial Sequence: GFP fusion
      protein

<400> SEQUENCE: 1 aagcttgcc atg ggc tgc ctc ggc aac agt aag acc gag gac cag cgc aac        51
          Met Gly Cys Leu Gly Asn Ser Lys Thr Glu Asp Gln Arg Asn
            1               5                  10 gag gag aag gcg cag cgc gag gcc aac aaa aag atc gag aag cag ctg          99
Glu Glu Lys Ala Gln Arg Glu Ala Asn Lys Lys Ile Glu Lys Gln Leu
 15                  20                  25                  30 cag aag gac aag cag gtc tac cgg gcc acg cac cgc ctg ctg ctg ctg         147
Gln Lys Asp Lys Gln Val Tyr Arg Ala Thr His Arg Leu Leu Leu Leu
                 35                  40                  45
```

```
ggt gct gga gag tct ggc aaa agc acc att gtg aag cag atg agg atc       195
Gly Ala Gly Glu Ser Gly Lys Ser Thr Ile Val Lys Gln Met Arg Ile
            50                  55                  60 cta cat gtt aat ggg ttt aac gga gag ggc ggc gaa gag gac gaa ttc       243
Leu His Val Asn Gly Phe Asn Gly Glu Gly Gly Glu Glu Asp Glu Phe
    65                  70                  75 gcc acc atg gtg agc aag ggc gag gag ctg ttc acc ggg gtg gtg ccc       291
Ala Thr Met Val Ser Lys Gly Glu Glu Leu Phe Thr Gly Val Val Pro
80                  85                  90 atc ctg gtc gag ctg gac ggc gac gta aac ggc cac aag ttc agc gtg       339
Ile Leu Val Glu Leu Asp Gly Asp Val Asn Gly His Lys Phe Ser Val
 95                 100                 105                 110 tcc ggc gag ggc gag ggc gat gcc acc tac ggc aag ctg acc ctg aag       387
Ser Gly Glu Gly Glu Gly Asp Ala Thr Tyr Gly Lys Leu Thr Leu Lys
                115                 120                 125 ttc atc tgc acc acc ggc aag ctg ccc gtg ccc tgg ccc acc ctc gtg       435
Phe Ile Cys Thr Thr Gly Lys Leu Pro Val Pro Trp Pro Thr Leu Val
            130                 135                 140 acc acc ctg acc tac ggc gtg cag tgc ttc agc cgc tac ccc gac cac       483
Thr Thr Leu Thr Tyr Gly Val Gln Cys Phe Ser Arg Tyr Pro Asp His
        145                 150                 155 atg aag cag cac gac ttc ttc aag tcc gcc atg ccc gaa ggc tac gtc       531
Met Lys Gln His Asp Phe Phe Lys Ser Ala Met Pro Glu Gly Tyr Val
    160                 165                 170 cag gag cgc acc atc ttc ttc aag gac gac ggc aac tac aag acc cgc       579
Gln Glu Arg Thr Ile Phe Phe Lys Asp Asp Gly Asn Tyr Lys Thr Arg
175                 180                 185                 190 gcc gag gtg aag ttc gag ggc gac acc ctg gtg aac cgc atc gag ctg       627
Ala Glu Val Lys Phe Glu Gly Asp Thr Leu Val Asn Arg Ile Glu Leu
                195                 200                 205 aag ggc atc gac ttc aag gag gac ggc aac atc ctg ggg cac aag ctg       675
Lys Gly Ile Asp Phe Lys Glu Asp Gly Asn Ile Leu Gly His Lys Leu
            210                 215                 220 gag tac aac tac aac agc cac aac gtc tat atc atg gcc gac aag cag       723
Glu Tyr Asn Tyr Asn Ser His Asn Val Tyr Ile Met Ala Asp Lys Gln
        225                 230                 235 aag aac ggc atc aag gtg aac ttc aag atc cgc cac aac atc gag gac       771
Lys Asn Gly Ile Lys Val Asn Phe Lys Ile Arg His Asn Ile Glu Asp
    240                 245                 250 ggc agc gtg cag ctc gcc gac cac tac cag cag aac acc ccc atc ggc       819
Gly Ser Val Gln Leu Ala Asp His Tyr Gln Gln Asn Thr Pro Ile Gly
255                 260                 265                 270 gac ggc ccc gtg ctg ctg ccc gac aac cac tac ctg agc acc cag tcc       867
Asp Gly Pro Val Leu Leu Pro Asp Asn His Tyr Leu Ser Thr Gln Ser
                275                 280                 285 gcc ctg agc aaa gac ccc aac gag aag cgc gat cac atg gtc ctg ctg       915
Ala Leu Ser Lys Asp Pro Asn Glu Lys Arg Asp His Met Val Leu Leu
            290                 295                 300 gag ttc gtg acc gcc gcc ggg atc act ctc ggc atg gac gag ctg tac       963
Glu Phe Val Thr Ala Ala Gly Ile Thr Leu Gly Met Asp Glu Leu Tyr
        305                 310                 315 aag tcc tct aga aac agc gat ggt gag aag gcc acc aaa gtg cag gac      1011
Lys Ser Ser Arg Asn Ser Asp Gly Glu Lys Ala Thr Lys Val Gln Asp
    320                 325                 330 atc aaa aac aac ctg aag gag gcc att gaa acc att gtg gcc gcc atg      1059
Ile Lys Asn Asn Leu Lys Glu Ala Ile Glu Thr Ile Val Ala Ala Met
335                 340                 345                 350 agc aac ctg gtg ccc ccc gtg gag ctg gcc aac cct gag aac cag ttc      1107
Ser Asn Leu Val Pro Pro Val Glu Leu Ala Asn Pro Glu Asn Gln Phe
                355                 360                 365
```

```
                                                           -continued
aga gtg gac tac att ctg agc gtg atg aac gtg cca aac ttt gac ttc      1155
Arg Val Asp Tyr Ile Leu Ser Val Met Asn Val Pro Asn Phe Asp Phe
            370                 375                 380 cca cct gaa ttc tat gag cat gcc aag gct ctg tgg gag gat gag gga      1203
Pro Pro Glu Phe Tyr Glu His Ala Lys Ala Leu Trp Glu Asp Glu Gly
        385                 390                 395 gtt cgt gcc tgc tac gag cgc tcc aac gag tac cag ctg atc gac tgt      1251
Val Arg Ala Cys Tyr Glu Arg Ser Asn Glu Tyr Gln Leu Ile Asp Cys
    400                 405                 410 gcc cag tac ttc ctg gac aag att gat gtg atc aag cag gcc gac tac      1299
Ala Gln Tyr Phe Leu Asp Lys Ile Asp Val Ile Lys Gln Ala Asp Tyr
415                 420                 425                 430 gtg cca agt gac cag gac ctg ctt cgc tgc cgc gtc ctg acc tct gga      1347
Val Pro Ser Asp Gln Asp Leu Leu Arg Cys Arg Val Leu Thr Ser Gly
            435                 440                 445 atc ttt gag acc aag ttc cag gtg gac aaa gtc aac ttc cac atg ttc      1395
Ile Phe Glu Thr Lys Phe Gln Val Asp Lys Val Asn Phe His Met Phe
        450                 455                 460 gat gtg ggc ggc cag cgc gat gaa cgc cgc aag tgg atc cag tgc ttc      1443
Asp Val Gly Gly Gln Arg Asp Glu Arg Arg Lys Trp Ile Gln Cys Phe
    465                 470                 475 aat gat gtg act gcc atc atc ttc gtg gtg gcc agc agc agc tac aac      1491
Asn Asp Val Thr Ala Ile Ile Phe Val Val Ala Ser Ser Ser Tyr Asn
480                 485                 490 atg gtc atc cgg gag gac aac cag acc aac cgt ctg cag gag gct ctg      1539
Met Val Ile Arg Glu Asp Asn Gln Thr Asn Arg Leu Gln Glu Ala Leu
495                 500                 505                 510 aac ctc ttc aag agc atc tgg aac aac aga tgg ctg cgt acc atc tct      1587
Asn Leu Phe Lys Ser Ile Trp Asn Asn Arg Trp Leu Arg Thr Ile Ser
            515                 520                 525 gtg atc ctc ttc ctc aac aag caa gat ctg ctt gct gag aag gtc ctc      1635
Val Ile Leu Phe Leu Asn Lys Gln Asp Leu Leu Ala Glu Lys Val Leu
        530                 535                 540 gct ggg aaa tcg aag att gag gac tac ttt cca gag ttc gct cgc tac      1683
Ala Gly Lys Ser Lys Ile Glu Asp Tyr Phe Pro Glu Phe Ala Arg Tyr
    545                 550                 555 acc act cct gag gat gcg act ccc gag ccc gga gag gac cca cgc gtg      1731
Thr Thr Pro Glu Asp Ala Thr Pro Glu Pro Gly Glu Asp Pro Arg Val
560                 565                 570 acc cgg gcc aag tac ttc atc cgg gat gag ttt ctg aga atc agc act      1779
Thr Arg Ala Lys Tyr Phe Ile Arg Asp Glu Phe Leu Arg Ile Ser Thr
575                 580                 585                 590 gct agt gga gat gga cgt cac tac tgc tac cct cac ttt acc tgc gcc      1827
Ala Ser Gly Asp Gly Arg His Tyr Cys Tyr Pro His Phe Thr Cys Ala
            595                 600                 605 gtg gac act gag aac atc cgc cgt gtc ttc aac gac tgc cgt gac atc      1875
Val Asp Thr Glu Asn Ile Arg Arg Val Phe Asn Asp Cys Arg Asp Ile
        610                 615                 620 atc cag cgc atg cat ctt cgc caa tac gag ctg ctc taagaaggga          1921
Ile Gln Arg Met His Leu Arg Gln Tyr Glu Leu Leu
    625                 630 acgcccaaat ttaattcagc cttaagcaca attaattaag agtgaaacgc aatcgtacaa   1981
gcagttgatc acccaccata gggcatgatc aacaccgcaa cctttcccctt ttctccccag  2041 tgattctgaa accccctct tcccttcagc ttgcttagat gttctctaga               2091

<210> SEQ ID NO 2
<211> LENGTH: 634
<212> TYPE: PRT
<213> ORGANISM: Artificial Sequence
<220> FEATURE:
```

<223> OTHER INFORMATION: Description of Artificial Sequence: GFP fusion
      protein

<400> SEQUENCE: 2

```
Met Gly Cys Leu Gly Asn Ser Lys Thr Glu Asp Gln Arg Asn Glu Glu
  1               5                  10                  15

Lys Ala Gln Arg Glu Ala Asn Lys Lys Ile Glu Lys Gln Leu Gln Lys
             20                  25                  30

Asp Lys Gln Val Tyr Arg Ala Thr His Arg Leu Leu Leu Leu Gly Ala
         35                  40                  45

Gly Glu Ser Gly Lys Ser Thr Ile Val Lys Gln Met Arg Ile Leu His
     50                  55                  60

Val Asn Gly Phe Asn Gly Glu Gly Gly Glu Glu Asp Glu Phe Ala Thr
 65                  70                  75                  80

Met Val Ser Lys Gly Glu Glu Leu Phe Thr Gly Val Val Pro Ile Leu
                 85                  90                  95

Val Glu Leu Asp Gly Asp Val Asn Gly His Lys Phe Ser Val Ser Gly
            100                 105                 110

Glu Gly Glu Gly Asp Ala Thr Tyr Gly Lys Leu Thr Leu Lys Phe Ile
        115                 120                 125

Cys Thr Thr Gly Lys Leu Pro Val Pro Trp Pro Thr Leu Val Thr Thr
130                 135                 140

Leu Thr Tyr Gly Val Gln Cys Phe Ser Arg Tyr Pro Asp His Met Lys
145                 150                 155                 160

Gln His Asp Phe Phe Lys Ser Ala Met Pro Glu Gly Tyr Val Gln Glu
                165                 170                 175

Arg Thr Ile Phe Phe Lys Asp Asp Gly Asn Tyr Lys Thr Arg Ala Glu
            180                 185                 190

Val Lys Phe Glu Gly Asp Thr Leu Val Asn Arg Ile Glu Leu Lys Gly
        195                 200                 205

Ile Asp Phe Lys Glu Asp Gly Asn Ile Leu Gly His Lys Leu Glu Tyr
    210                 215                 220

Asn Tyr Asn Ser His Asn Val Tyr Ile Met Ala Asp Lys Gln Lys Asn
225                 230                 235                 240

Gly Ile Lys Val Asn Phe Lys Ile Arg His Asn Ile Glu Asp Gly Ser
                245                 250                 255

Val Gln Leu Ala Asp His Tyr Gln Gln Asn Thr Pro Ile Gly Asp Gly
            260                 265                 270

Pro Val Leu Leu Pro Asp Asn His Tyr Leu Ser Thr Gln Ser Ala Leu
        275                 280                 285

Ser Lys Asp Pro Asn Glu Lys Arg Asp His Met Val Leu Leu Glu Phe
290                 295                 300

Val Thr Ala Ala Gly Ile Thr Leu Gly Met Asp Glu Leu Tyr Lys Ser
305                 310                 315                 320

Ser Arg Asn Ser Asp Gly Glu Lys Ala Thr Lys Val Gln Asp Ile Lys
                325                 330                 335

Asn Asn Leu Lys Glu Ala Ile Glu Thr Ile Val Ala Ala Met Ser Asn
            340                 345                 350

Leu Val Pro Pro Val Glu Leu Ala Asn Pro Glu Asn Gln Phe Arg Val
        355                 360                 365

Asp Tyr Ile Leu Ser Val Met Asn Val Pro Asn Phe Asp Phe Pro Pro
    370                 375                 380

Glu Phe Tyr Glu His Ala Lys Ala Leu Trp Glu Asp Glu Gly Val Arg
385                 390                 395                 400
```

-continued

```
Ala Cys Tyr Glu Arg Ser Asn Glu Tyr Gln Leu Ile Asp Cys Ala Gln
            405                 410                 415

Tyr Phe Leu Asp Lys Ile Asp Val Ile Lys Gln Ala Asp Tyr Val Pro
        420                 425                 430

Ser Asp Gln Asp Leu Leu Arg Cys Arg Val Leu Thr Ser Gly Ile Phe
            435                 440                 445

Glu Thr Lys Phe Gln Val Asp Lys Val Asn Phe His Met Phe Asp Val
        450                 455                 460

Gly Gly Gln Arg Asp Glu Arg Arg Lys Trp Ile Gln Cys Phe Asn Asp
465                 470                 475                 480

Val Thr Ala Ile Ile Phe Val Val Ala Ser Ser Tyr Asn Met Val
                485                 490                 495

Ile Arg Glu Asp Asn Gln Thr Asn Arg Leu Gln Glu Ala Leu Asn Leu
            500                 505                 510

Phe Lys Ser Ile Trp Asn Asn Arg Trp Leu Arg Thr Ile Ser Val Ile
        515                 520                 525

Leu Phe Leu Asn Lys Gln Asp Leu Leu Ala Glu Lys Val Leu Ala Gly
    530                 535                 540

Lys Ser Lys Ile Glu Asp Tyr Phe Pro Glu Phe Ala Arg Tyr Thr Thr
545                 550                 555                 560

Pro Glu Asp Ala Thr Pro Glu Pro Gly Glu Asp Pro Arg Val Thr Arg
                565                 570                 575

Ala Lys Tyr Phe Ile Arg Asp Glu Phe Leu Arg Ile Ser Thr Ala Ser
            580                 585                 590

Gly Asp Gly Arg His Tyr Cys Tyr Pro His Phe Thr Cys Ala Val Asp
        595                 600                 605

Thr Glu Asn Ile Arg Arg Val Phe Asn Asp Cys Arg Asp Ile Ile Gln
    610                 615                 620

Arg Met His Leu Arg Gln Tyr Glu Leu Leu
625                 630

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Tyr Glu Leu Leu
  1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Cys Gly Leu Phe
  1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
```

```
                            peptide

<400> SEQUENCE: 5

Glu Cys Gly Leu Tyr
  1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Cys Gly Leu Tyr
  1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Tyr Asn Leu Val
  1               5

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 8
ggaattcatg agcaagggcg aggaactg                                      28

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 9
gctctagacg acttgtacag ctcgt                                         25

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 10
gggtaccatg ggctgcctcg gcaaca                                        26

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 11
```

```
ggaattcgtc ctcttcgccg cccttct                                                27

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 12
cagagctgga caagtccaac agcgatggtg agaa                                        34
```